United States Patent
Paek

(10) Patent No.: US 6,767,560 B2
(45) Date of Patent: Jul. 27, 2004

(54) FABRICATION METHOD OF ORAL CARE COMPOSITION

(76) Inventor: Paul H Paek, 950 S. Western Ave., Los Angeles, CA (US) 90006

( * ) Notice: Subject to any disclaimer, the term of this patent is extended or adjusted under 35 U.S.C. 154(b) by 127 days.

(21) Appl. No.: 10/051,744

(22) Filed: Jan. 22, 2002

(65) Prior Publication Data

US 2003/0157206 A1 Aug. 21, 2003

(51) Int. Cl.$^7$ .......................... A61K 31/26; A61K 31/16
(52) U.S. Cl. ........................... 424/725; 424/48; 424/49; 424/58; 424/195.1; 424/773
(58) Field of Search .............................. 424/48, 49, 58, 424/195.1, 725, 773

(56) References Cited

U.S. PATENT DOCUMENTS

| 5,180,575 A | 1/1993 | Ha et al. | 404/49 |
| 2002/0039559 A1 * | 4/2002 | Paek | 424/48 |

FOREIGN PATENT DOCUMENTS

| CN | 1115248 | | 1/1996 |
| CN | 1192896 | * | 3/1997 |
| CN | 1192896 | | 9/1998 |
| CN | 1192898 A | | 9/1998 |
| CN | 1221626 | * | 7/1999 |
| DE | 04221103 | | 1/1993 |
| GB | 1438205 | | 8/1974 |
| JP | 58057320 A | | 4/1983 |
| JP | 58213706 | | 12/1983 |
| JP | 09-031094 | * | 2/1997 |
| JP | 63048208 A | | 11/1997 |
| JP | 361122221 A | | 7/1999 |
| WO | WO 9921425 | | 5/1999 |
| WO | WO 02/100422 | * | 12/2002 |

OTHER PUBLICATIONS

Dueker et al. "Effects of extracts from cimicifuga . . . " Biosis 1992:31936 (1992).*
Zou et al. "Isolation and characterization . . . " CA 123:2060 (1995).*
Liske et al. "Therapeutic efficacy . . . " 1998:216584 (1998).*
Burdette et al. "Black cohosh . . . " Biosis 2003:26424 (2003).*
Burdette et al. "Black cohosh acts as a mixed . . . " Biosis 2003:483768 (2003).*
Molony et al., Complete Guide to Chinese Herbal Medicine, Berkley Publishing Group, NY, p. 99.
J. of Dental Research (1993), vol. 72, No. Abstr. 458, Spec. Issue, p 61. Brockman et al., Antimicrobial activity of Zanthoxylum nitidum plant alkaloid against oral pathogens.

* cited by examiner

Primary Examiner—Celia Chang
(74) Attorney, Agent, or Firm—Park & Sutton LLP; John K. Park

(57) ABSTRACT

A fabrication method of an oral care composition comprising the steps of drying a Cimicifuga root, soaking the dried Cimicifuga root in a vinegar for a predetermined time period, and drying the vinegar-soaked Cimicifuga root. The vinegar-soaked then dried Cimicifuga root, a salt and a water are admixed at a sequential weight ratio of about 10% to 40%, about 10% to 40% and about 30% to 50%. The admixture of the Cimicifuga root, the salt and the water are evaporated to obtain a Cimicifuga-salt concentration and then Cimicifuga root fibers are removed from the Cimicifuga-salt concentration.

17 Claims, No Drawings

FABRICATION METHOD OF ORAL CARE COMPOSITION

BACKGROUND OF THE INVENTION

The present invention relates to an oral care composition applicable to oral hygiene products such as toothpaste and mouth detergent. More particularly, the present invention relates to a fabrication method of an oral care composition by use of salt and herbal extracts for treatment efficacy on periodontal diseases.

Oral care products including dentifrice are known to contain components such as sodium chlorides, antiplasmin agents, allantoin derivatives, vitamines, amino acids and others. Since the selection of the components is substantially influenced by target taste, target flavor and target sweetness, the sodium chloride which is known as effective in oral hygiene has suffered from artificial deformation in composition when used for different products. For example, a peppermint oil and a spearmint oil are used as a flavoring agent to decrease salty taste. Or sodium lauryl sulphate is used as a foaming agent to improve foaming properties. Also, tranexamic acid, aluminium chlorohydroxy allantonate and tocopherol acetate in admixture with sodium chloride are used to treat or prevent periodontal diseases. However, no treatment or prevention effects against periodontal diseases are expected other than slight improvements in taste and flavor. U.S. Pat. No. 5,180,575 discloses a bamboo-salt as a composition for oral care products such as toothpaste. Still, treatment or prevention effects against periodontal disease are hardly expected.

In consideration of the foregoing disadvantages, the present inventor has conducted extensive clinical experiments on the combination of salt and herbal extracts for substantial improvement on prevention or treatment effects against periodontal disease while enhancing oral hygiene. Although it took a considerable time period to compare treatment or prevention effects from experimental herbs which are widely being used in oriental herbal treatments, it was eventually discovered that a Cimicifuga-salt preferably in admixture of Coptis and zanthoxylin produces substantial treatment effects against periodontal diseases such as gingivitis or dental caries.

A Cimicifuga-salt consists of a living salt and Cimicifuga extracts. The living salt is obtained by melting pure bay salt at a high temperature or preferably at about 1,000° C. for about 48 hours. The living salt is believed to have treatment effect since it reserves condensed energy and osmotic pressure at the melting stage which substantially enhance sterilization effects. Also, it has treatment effects against gum bleeding, edema, inflammation, halitosis, tooth decay and serious periodontal diseases (Donguebogam, Korean Medicinal Book). The nostrum of the living salt is further demonstrated in Sinkum (Living Salt) Therapy for Healthy Life and Living Salt Therapy Sink (by Kyound Jin Park, 1985), and Living Salt Diet for Diabetics, Folklore Living Salt Therapy to Revive Liver Cells (by Il Sun Oh, 1993). The living salt has been used by Oriental doctors specialized in alternative medicine for hundreds of years in Korea.

Commercially available Cimicifuga herb contains cimitin $C_{20}H_{34}O_7$, $Et_2O$, BuOH, cimicifugin, salicylic acid, cimigenol, 25-O-methylcimigenol-3-xyloside, cimigol, dahurinol, isodahurinol, acerinol, 24-O-acetylacerinol, cimicifugoside, cimicifugenin, 26-O-methylcimifugoside, ciminifugenin A, 26-O-methylcimifugenin A, cimifugenol, friedelin, b-sitosterol, khellol, amminol, 3,4-dimethylcinnamic acid, ferulic acid, iso-ferulic acid, dahurinol, coumarin and others. The Cimicifuga herb alleviates pain and inhibits the growth of tuberculosis viruses and dermal fungi in vitro. In the human body, $Et_2O$ serves as sedatives and suppresses edema. BuOH reduces bodily temperature and serves as pain relievers, edema suppressants, and anti-ulceratives.

Consequently, it is understood that the Cimicifuga-salt obtained by combining the living salt and Cimicifuga extracts is effective for detoxication, fever reduction, anti-inflammation, improvement in the cytoginic function, antisepsis, cancer prevention, sterilization, cold symtoms, various anemisa, and hypotension.

Coptis herb is commerically available and includes alkaloid, berberine (4–7%), Coptisine, jatoerrhizine, palmitine, magnoflorine, ferulic acid and others. In pharmacological actions, the Coptis herb relieves bodily fever, prevents dehydration and toxication. Among the components, the berberine and Coptisine are known to serve as antibiotics, laxatives, anti-inflammatory agents and stytics, and stop diarrhea.

Commercially available zanthoxylin is classified to belong to zanthoxylum piperitum and contains sanshool $C_{16}H_{27}ON$, sanshoon $C_{16}H_{25}ON$, sanshoamide, geraniol and others. Zanthoxylin serves to warm bodily digestive organs, relieve pain, treat diarrhea and kill intestinal worms. In vitro, it suppresses gram-negatives such as dysentery viruses, and gram-positive aerobic viruses such as staphylococcus aureus and it also kills round worms in swine.

So it is readily understood that the Cimicifuga-salt alone or in admixture of Coptis and zanthoxylin enhances treatment or prevention effect against periodontal diseases such as gingivitis, dental caries, oral abscess, gum inflammation, tooth decay and other gum or tooth related diseases.

SUMMARY OF THE INVENTION

The present invention is contrived to overcome the disadvantages in the prior arts. Therefore, it is an object of the present invention to provide a fabrication method of an oral care composition which substantially improves treatment efficacy on periodontal diseases by using a combination of salt and herbal extracts.

To achieve the above-described object, the fabrication method of an oral care composition according to the present invention comprises the steps of drying a Cimicifuga root, soaking the dried Cimicifuga root in a vinegar for a predetermined time period, and drying the vinegar-soaked Cimicifuga root. The vinegar-soaked then dried Cimicifuga root, a salt and a water are admixed at a sequential weight ratio of about 10% to 40%, about 10% to 40% and about 30% to 50%. Then, the admixture of the Cimicifuga root, the salt and the water are evaporated to obtain a Cimicifuga-salt concentration.

For a better version, Cimicifuga root fibers are removed from the Cimicifuga-salt concentration. Preferably, each step for fabricating the oral care composition is performed within a non-metallic container. The vinegar is obtained by a fermentation process from a brown rice. A filler material including a sodium chloride may be added to the Cimicifuga-salt concentration. The method may further comprise an additional step of incorporating the oral care composition with conventional oral hygiene compositions selected from a toothpaste, a mouth detergent, a mouthwash, a chewing gum, or and a gum massage cream.

In an embodiment, a dried Coptis root is further included in the fabrication steps so that the dried Cimicifuga root and the dried Coptis root are admixed at a substantially equivalent ratio in weight. Said each dried Cimicifuga root and Coptis root are soaked in a vinegar for a predetermined time period and then dried. The vinegar-soaked and then dried Cimicifuga-Coptis root admixture, a salt and a water at a sequential weight ratio of about 10% to 40%, about 10% to 40% and about 30% to 50%. The admixture of the Cimicifuga-Coptis root admixture, the salt and the water are evaporated to obtain a Cimicifuga-Coptis-salt concentration. Cimicifuga root fibers are removed from the Cimicifuga-Coptis-salt concentration.

As another embodiment, an oral care composition comprises a Cimicifuga root and a Coptis root each substantially dried, soaked in a vinegar, and then dried for a predetermined time period. The dried, vinegar-soaked and then dried Cimicifuga root and Coptis root are formed at a substantially equivalent ratio in weight. Further comprised for the oral care composition is a salt and a water so that the dried, vinegar-soaked and then dried Cimicifuga-Coptis root, the salt and the water are admixed at a sequential weight ratio of about 10% to 40%, about 10% to 40% and about 30% to 50%. The admixture is evaporated to a Cimicifuga-salt concentration, wherein Cimicifuga root fibers are removed from the Cimicifuga-salt concentration to form the oral care composition.

The advantages of the present invention are numerous in that (1) the fabrication method of an oral care composition enables Cimicifuga and Coptis extracts to directly apply to interior of a user's mouth together with nostrum living salt in a daily required formulation such as toothpaste, thereby enhancing prevention or treatment effects against periodontal diseases; (2) the oral care composition allows oriental herbal therapeutic treatment to get effectively mixed with daily hygienic activities such as oral cleansing as an alternative to dentist-allergic periodontal patients; and (3) the oral care composition effectively prevents mouth diseases to serve as a reliable alternative therapy against mouth cancer which is ranked the $8^{th}$ highest death rate among the U.S. cancer patients.

Although the present invention is briefly summarized, the fuller understanding of the invention can be obtained by the following drawings, detailed description and appended claims.

THE DETAILED SPECIFICATION OF THE PREFERRED EMBODIMENTS

A fabrication method of an oral care composition according to the present invention comprises the steps of drying Cimicifuga root, soaking the dried Cimicifuga root in a vinegar for a predetermined time period, and then drying the vinegar-soaked Cimicifuga root. Here, the Cimicifuga root is better harvested in September and October. The harvested Cimicifuga root is cleaned using a cold water, preferably a running cold water as an initial hygienic process. The vinegar may be obtained by a fermentation process from a brown rice. Selectively, the vinegar may be diluted depending on a required degree of sterilization.

The vinegar-soaked then dried Cimicifuga root, a salt and a water are admixed at a sequential weight ratio of about 10% to 40%, about 10% to 40% and about 30% to 50%. Then, the admixture of the Cimicifuga root, the salt and the water are evaporated to obtain a Cimicifuga-salt concentration. Thereafter, Cimicifuga root fibers are removed from the Cimicifuga-salt concentration. Alternately, the sequential weight ratio of the vinegar-soaked then dried Cimicifuga root, the salt and the water may be about 40%, about 30%, and about 30%.

Each step for the oral care composition fabrication is performed within a non-metallic container to better preserve original ingredients in the Cimicifuga root. Also, each drying step is better performed on an oak panel layered over a heated floor. The heated floor is prepared by red soil. Here, it is preferred that the oak panel is about 1.0 centimeter in thickness. The temperature for each drying step may be about 55 Celsius degrees to prevent fungus generation and at the same time fully take advantage of hygienic performance in oak itself. Each drying step is implemented for at least one week or about 170 hours.

In a preferred embodiment, a filler material is added to the Cimicifuga-salt concentration. The filler material substantially includes a sodium chloride. The method may comprise an additional step of incorporating the thusly constituted composition with conventional oral hygiene compositions selected from a toothpaste, a mouth detergent, a mouthwash, a chewing gum, or a gum massage cream.

For a better performance, a fabrication method of an oral care composition comprising the steps of drying a Cimicifuga root and a Coptis root, admixing the dried Cimicifuga root and the dried Coptis root at a substantially equivalent ratio in weight, soaking said each dried Cimicifuga and Coptis root in a vinegar for a predetermined time period, drying the vinegar-soaked Cimicifuga-Coptis root admixture, and admixing the vinegar-soaked then dried Cimicifuga-Coptis root admixture, a salt and a water at a sequential weight ratio of about 10% to 40%, about 10% to 40% and about 30% to 50%. The admixture of the Cimicifuga-Coptis root admixture, the salt and the water are then evaporated to obtain a Cimicifuga-Coptis-salt concentration. Then, Cimicifuga root fibers are removed from the Cimicifuga-Coptis-salt concentration.

The sequential weight ratio of the vinegar-soaked then dried Cimicifuga-Coptis root, the salt and the water is about 40%, about 30%, and about 30%. Alternately, the sequential weight ratio of the vinegar-soaked then dried Cimicifuga-Coptis root, the salt and the water is about 20%, about 40%, and about 40%.

In another embodiment, an oral care composition is fabricated according to the method as disclosed above. That is, the oral care composition according to the present invention comprises a Cimicifuga root and a Coptis root each substantially dried, soaked in a vinegar, and then dried for a predetermined time period, wherein the dried, vinegar-soaked and then dried Cimicifuga root and Coptis root are formed at a substantially equivalent ratio in weight. The composition further comprises a salt and a water so that the dried, vinegar-soaked and then dried Cimicifuga-Coptis root, the salt and the water are admixed at a sequential weight ratio of about 10% to 40%, about 10% to 40% and about 30% to 50%. The admixture is evaporated to a Cimicifuga-salt concentration, and Cimicifuga root fibers are removed from the Cimicifuga-salt concentration to form the oral care composition.

According to the composition, the vinegar-soaked then dried Cimicifuga root, the salt and the water is about 40%, about 30%, and about 30%. Alternately, the vinegar-soaked then dried Cimicifuga root, the salt and the water is about 20%, about 40%, and about 40%. The vinegar is preferably obtained by a fermentation from a brown rice.

The salt required for the oral care composition is a living salt obtained by melting a pure bay salt at about 1000° C. for about 24 hours. The composition solely including the Cimicifuga-salt may further comprise foaming agents, wetting agents, sweetening agents, flavoring agents, polishing agents, preservatives, binders and pharmacologically active agents. Alternately, the composition may comprise solely the admixture of the Cimicifuga-salt, the Coptis, and the zanthoxylin. The composition solely including the Cimicifuga-salt, Coptis and zanthoxylin may further comprise foaming agents, wetting agents, sweetening agents, flavoring agents, polishing agents, preservatives, binders and pharmacologically active agents.

The oral care composition according to the present invention may be incorporated in oral hygiene products such as a toothpaste, a mouth detergent, a tooth powder, a mouth spray, a chewing gum, a gum massage cream, or a denture cleansing formulation. Here, the composition of a Cimicifuga-salt alone or in admixture of Coptis and zanthoxylin is also called Byczenol (a trademark to be registered by the inventor).

To obtain the best performance, it is recommended that the composition of the Cimicifuga-salt alone or in admixture of Coptis and zanthoxylin account for about 30% in a classic toothpaste. Selectively, the composition rate can be raised up to 80% for a stronger treatment effect against periodontal diseases. However, the ratio or amount of Cimicifuga-salt along or in admixture of Coptis and zanthoxylin may be adjusted depending upon treatment or prevention targets.

An effective amount of components for a conventional toothpaste may be mixed with the composition according to the present invention. For example, there are polishing agents such as dicalcium, phosphate, silicone dioxide aluminum hydroxide, or calcium carbonate; humectants such as sorbitol, glycerin, or polyethylene glycol; foaming agents such as sodium alkylsulphate, or polyoxyethylene-polyoxypropylene condensation polymer; sweetening agent such as saccharin, or aspartame; flavoring agents such as peppermint oil, or spearmint; preservatives such as methyl paraoxy benzoic acid; therapeutic agents such as sodium fluoride, chlorhexidine, tranexamic acid, or allantoin; binders; and others.

The oral care composition according to the present invention will be further described with reference to the accompanying Examples and Comparative Examples.

COMPARATIVE EXAMPLES 1 TO 4 AND EXAMPLES A, B

Toothpaste components were prepared as shown in Table 1

TABLE 1

| Components | Comparative Examples | | | | Examples | |
|---|---|---|---|---|---|---|
| | 1(%) | 2(%) | 3(%) | 4(%) | A (%) | B (%) |
| Byczenol-A* | — | — | — | — | 10.0 | 20.0 |
| Dicalcium phosphate | 40.0 | 40.0 | 40.0 | 40.0 | 30.0 | 20.0 |
| Non-crystalline sorbitol solution | 25.0 | 25.0 | 25.0 | 25.0 | 15.0 | 15.0 |
| Bamboo-salt | 2.0 | 5.0 | — | — | — | — |
| Sodium chloride | — | — | 1.0 | 1.5 | — | — |
| Aluminum chlorohydroxy allantoinate | — | — | 0.1 | 0.1 | — | — |
| Tocopherol acetate | — | — | 0.1 | 0.1 | — | — |
| Tranexamic acid | — | — | 0.1 | 0.1 | — | — |
| Sodium glutamate | — | — | 0.01 | 0.01 | — | — |
| Sodium alkylsulphate | 2.0 | 2.0 | 2.0 | 2.0 | — | — |
| Sodium saccharin | 1.0 | 1.0 | 1.0 | 1.0 | — | — |
| Sodium carboxymethyl cellulose | 1.0 | 1.0 | 1.0 | 1.0 | — | — |
| Flavoring agent | 0.8 | 0.8 | 0.8 | 0.8 | — | — |
| By adding diluted water, up to | 100 | 100 | 100 | 100 | 100 | 100 |
| U.V. spectrophotometer transmittance | 20.0 | 30.0 | 10.0 | 10.0 | 50.0 | 70.0 |

*Byczenol-A is Cimicifuga-salt

COMPARATIVE EXAMPLES 5 TO 8 AND EXAMPLES C TO F

Toothpaste components were prepared as shown in Table 2

TABLE 2

| Components | Comparative Examples (%) | | | | Examples (%) | | | |
|---|---|---|---|---|---|---|---|---|
| | 5(%) | 6(%) | 7(%) | 8(%) | C (%) | D (%) | E (%) | F (%) |
| Byczenol-B* | — | — | — | — | 25.0 | 40.0 | 55.0 | 70.0 |
| Dicalcium phosphate | 35.0 | 35.0 | 35.0 | 23.0 | — | — | — | — |
| Calcium carbonate | — | — | — | — | — | — | — | — |
| Precipitated silica | — | — | — | — | — | — | — | — |
| Anhydrous silicic acid | — | — | — | — | — | — | — | — |
| Non-crystalline sorbitol solution | — | — | — | — | — | — | — | — |
| Sorbitol solution | — | — | — | — | — | — | — | — |
| Glycerin | — | — | — | — | 35.0 | 30.0 | 20.0 | 15.0 |
| Sodium chloride | 10.0 | — | — | — | — | — | — | — |
| Bamboo-salt | 0.5 | 5.0 | 10.0 | 30.0 | — | — | — | — |
| Tranexamic acid | 0.05 | 0.05 | 0.05 | 0.05 | — | — | — | — |

TABLE 2-continued

|  | Comparative Examples (%) | | | | Examples (%) | | | |
| --- | --- | --- | --- | --- | --- | --- | --- | --- |
| Components | 5(%) | 6(%) | 7(%) | 8(%) | C (%) | D (%) | E (%) | F (%) |
| Aluminum chlorohydroxy allantoinate | 0.1 | 0.1 | 0.1 | 0.1 | — | — | — | — |
| Tocopherol acetate | 0.1 | 0.1 | 0.1 | 0.1 | — | — | — | — |
| 5-amino caproic acid | 0.05 | 0.05 | 0.05 | 0.05 | — | — | — | — |
| Sodium alkysulphate | 2.0 | 2.0 | 2.0 | 2.0 | — | — | — | — |
| Sugar-fatty acid ester | — | — | — | — | — | — | — | — |
| N-acyl glutamate | — | — | — | — | — | — | — | — |
| Magnesium chloride | 0.05 | 0.05 | 0.1 | 0.05 | — | — | — | — |
| Trimagnesium phosphate | 0.05 | 0.05 | 0.05 | 0.05 | — | — | — | — |
| Sodium saccharin | 0.1 | 0.1 | 0.1 | 0.1 | — | — | — | — |
| Methyl Paraben | 0.05 | 0.05 | 0.05 | 0.05 | — | — | — | — |
| Sodium carboxymethyl Cellulose | 0.8 | 0.8 | 0.8 | 0.6 | — | — | — | — |
| Flavoring agent | 0.1 | 0.1 | 0.1 | 0.1 | — | — | — | — |
| By adding diluted water, up to | 100 | 100 | 100 | 100 | 100 | 100 | 100 | 100 |

*Byczenol-B is Cimicifuga-salt admixed with Coptis and zanthoxylin

EXPERIMENTAL TEST AND RESULTS THEREOF

Several groups of thirty (30) persons (between age 20 and age 55) suffering from halitosis (1st group), teeth sour (2nd group), gum bleeding (3rd group), gingivitis (4th group) and toothache (5th group) were tested three times a day for fifteen (15) days. The thirty participants brushed their teeth for about three minutes each time during the test period. The first group of thirty persons used the toothpastes containing the composition according to the present invention. The second group of the other thirty persons used conventional tooth pastes as described in the above Comparative Examples. The test results are as shown in Table 3.

TABLE 3

| Toothpaste Examples | Byczenol ratio | No. of Healed Persons per 30 Participants (%) | | | | |
| --- | --- | --- | --- | --- | --- | --- |
| | | I* | II* | III* | IV* | V* |
| Example C | 25% | 25 (83.3) | 26 (86.7) | 25 (83.3) | 26 (86.7) | 26 (86.7) |
| Example D | 40% | 26 (86.7) | 27 (90.0) | 27 (90.0) | 27 (90.0) | 27 (90.0) |
| Example E | 55% | 28 (93.3) | 29 (96.7) | 28 (93.3) | 28 (93.3) | 28 (93.3) |
| Example F | 70% | 29 (96.7) | 30 (100.0) | 29 (96.7) | 29 (96.7) | 29 (96.7) |
| Comp. 3 | 0% | 1 (3.3) | 3 (10.0) | 2 (6.7) | 2 (6.7) | 3 (10.0) |
| Comp. 4 | 0% | 0 (0.0) | 2 (6.7) | 1 (3.3) | 3 (10.0) | 2 (6.7) |
| Comp. 5 | 0% | 2 (6.7) | 0 (0.0) | 0 (0.0) | 2 (6.7) | 1 (3.3) |
| Comp. 6 | 0% | 2 (6.7) | 0 (0.0) | 1 (3.3) | 2 (6.7) | 1 (3.3) |

*Type of Participants Healed by Toothpaste Treatment
I:: participants with haliosis
II: participants with teeth sour
III: participants with gum bleeding
IV: participants with gingivitis
V: participants with toothache Table 3 demonstrates treatment effects of the toothpaste containing the oral care composition according to the present invention. As shown therein, the weight of the Cimicifuga-salt alone or in admixture of Coptis and zanthoxylin (Byczenol) is preferred to account for about 25% to 70% of a toothpaste of conventional components.

EXAMPLE G

| Mouth Detergent | |
| --- | --- |
| Ethanol (90%) | 20.0% |
| Glycerine (98%) | 10.0% |
| Polyxyethylene-polyoxypropylene Copolymer | 1.0% |
| Tranexamic acid | 0.05% |
| Byczenol | 10.0% |
| Sodium saccharin | 01% |
| Flavoring agent | 1.0% |
| By adding distilled water up to | 100.0.% |

EXAMPLE H

| Mouthwash | |
| --- | --- |
| Sodium bicarbonate | 20.0% |
| Stannic acid | 18.0% |
| Sodium sareosinate-coconut oil | 5.0% |
| Sodium lauryl sulfate | 5.0% |
| Benzalkonium chloride | 2.0% |
| EDTA | 5.0% |
| Sodium tripolyphosphate | 14.0% |
| Polyethylene glycol | 2.0% |
| Byczenol | 24.0% |
| Flavoring agent | 5.0% |

EXAMPLE I

| Chewing gum | |
| --- | --- |
| Gum base | 15.0% |
| Sorbitol | 30.0% |
| Manniol | 12.0% |
| Glycerine | 13.0% |
| Lecithin | 0.5% |
| Sweetening agent | 2.0% |
| Byczenol | 26.0% |
| Flavoring agent | 1.5% |

EXAMPLE J

| Gum Massage Cream | |
| --- | --- |
| Glycerol monolaurate | 3.0% |
| Oleic alcohlate | 5.0% |
| Polyethylene glycol | 15.0% |
| White Vaseline | 3.0% |
| Monosodium N-palmitic glutamate | 5.0% |
| Hydroxyethyl cellulose | 5.0% |
| Tocopherol acetate | 0.1% |
| Byczenol | 10.0% |
| Sweetening agent | 0.2% |
| Aluminum chlorohydroxy allantoinate | 3.0% |
| Flavoring agent | 0.3% |
| By adding distilled water up to | 100.0% |

As demonstrated above, the oral care composition according to the present invention prevents or treats periodontal diseases in a reliable healing rate.

An advantage of the present invention is to enable Cimicifuga and Coptis extracts to directly apply to interior of a user's mouth together with nostrum living salt in a daily required formulation such as toothpaste, thereby enhancing prevention or treatment effects against periodontal diseases. Further, the oral care composition allows oriental herbal therapeutic treatment to get effectively mixed with daily hygienic activities such as oral cleansing as an alternative to dentist-allergic periodontal patients. In addition, the oral care composition effectively prevents mouth diseases to serve as a reliable alternative therapy against mouth cancer which is ranked the $8^{th}$ highest death rate among the U.S. cancer patients.

Although the invention has been described in considerable detail with reference to certain preferred versions thereof, other versions are possible by converting the aforementioned construction. Therefore, the scope of the invention shall not be limited by the specification specified above and the appended claims.

What is claimed is:

1. A fabrication method of an oral care composition comprising the steps of:
   a) drying a Cimicifuga root;
   b) soaking the dried Cimicifuga root in a vinegar for predetermined time period;
   c) drying the vinegar-soaked Cimicifuga root;
   d) admixing the vinegar-soaked then dried Cimicifuga root, a salt and a water at a sequential weight ratio of about 10% to 40%, about 10% to 40% and about 30% to 50%;
   e) evaporating the admixture of the Cimicifuga root, the salt and the water to obtain a Cimicifuga-salt concentration; and
   f) removing Cimicifuga root fibers from the Cimicifuga-salt concentration.

2. The method of claim 1 wherein said each step is performed within a non-metallic container.

3. The method of claim 1 wherein said each drying step a) and c) is performed on an oak panel layered over a heated floor.

4. The method of claim 1 wherein, in the step d, the sequential weight ratio of the vinegar-soaked then dried Cimicifuga root, the salt and the water is about 40%, about 30%, and about 30%.

5. The method of claim 1 wherein the vinegar is obtained by a fermentation process from a brown rice.

6. The method of claim 1 further comprising, after the step f), adding a filler material to the Cimicifuga-salt concentration.

7. The method of claim 6 wherein the filler material comprises a sodium chloride.

8. The method of claim 1 further comprising an additional step of incorporating the oral care composition with conventional oral hygiene compositions selected from a toothpaste, a mouth detergent, a mouthwash, a chewing gum, or a gum massage cream.

9. A fabrication method of an oral care composition comprising the steps of:
   a) drying a Cimicifuga root and a Coptis root;
   b) admixing the dried Cimicifuga root and the dried Coptis root at a substantially equivalent ratio in weight;
   c) soaking said each dried Cimicifuga and Coptis root in a vinegar for a predetermined time period;
   d) drying the vinegar-soaked Cimicifuga-Coptis root admixture;
   e) admixing the vinegar-soaked then dried Cimicifuga-Coptis root admixture, a salt and a water at a sequential weight ratio of about 10% to 40%, about 10% to 40% and about 30% to 50%;
   f) evaporating the admixture of the Cimicifuga-Coptis root admixture, the salt and the water to obtain a Cimicifuga-Coptis-salt concentration; and
   g) removing Cimicifuga root fibers from the Cimicifuga-Coptis-salt concentration.

10. The method of claim 9 wherein, in the step e), the sequential weight ratio of the vinegar-soaked then dried Cimicifuga-Coptis root, the salt and the water is about 40%, about 30%, and about 30%.

11. The method of claim 9 wherein, in the step e), the sequential weight ratio of the vinegar-soaked then dried Cimicifuga-Coptis root, the salt and the water is about 20%, about 40%, and about 40%.

12. The method of claim 9 wherein said each step is performed within a non-metallic container.

13. The method of claim 9 wherein said each drying step a) and d) is performed on an oak panel layered over a heated floor.

14. The method of claim 1 wherein the vinegar is obtained by a fermentation process from a brown rice.

15. The method of claim 9 further comprising, after the step g), adding a filler material to the Cimicifuga-salt concentration.

16. The method of claim 15 wherein the filler material comprises a sodium chloride.

17. The method of claim 1 further comprising an additional step of incorporating the oral care composition with conventional oral hygiene compositions selected from a toothpaste, a mouth detergent, a mouthwash, a chewing gum, or a gum massage cream.

* * * * *